United States Patent
Wilson et al.

(10) Patent No.: US 12,268,724 B2
(45) Date of Patent: *Apr. 8, 2025

(54) METHODS AND COMPOSITIONS FOR THE PREVENTION OR TREATMENT OF BARTH SYNDROME

(71) Applicant: Stealth BioTherapeutics Inc., Needham, MA (US)

(72) Inventors: D. Travis Wilson, Needham, MA (US); Mark Bamberger, Needham, MA (US)

(73) Assignee: Stealth BioTherapeutics Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/454,319

(22) Filed: Aug. 23, 2023

(65) Prior Publication Data

US 2024/0156892 A1 May 16, 2024

Related U.S. Application Data

(63) Continuation of application No. 17/371,475, filed on Jul. 9, 2021, now Pat. No. 11,771,734, which is a continuation of application No. 16/929,370, filed on Jul. 15, 2020, now Pat. No. 11,083,772, which is a continuation of application No. 15/626,255, filed on Jun. 19, 2017, now Pat. No. 11,083,771, which is a continuation of application No. 14/771,408, filed as application No. PCT/US2014/019622 on Feb. 28, 2014, now Pat. No. 9,687,519.

(60) Provisional application No. 61/839,753, filed on Jun. 26, 2013, provisional application No. 61/771,534, filed on Mar. 1, 2013, provisional application No. 61/771,642, filed on Mar. 1, 2013.

(51) Int. Cl.
| | | |
|---|---|---|
| *A61K 38/00* | (2006.01) | |
| *A61K 38/06* | (2006.01) | |
| *A61K 38/07* | (2006.01) | |
| *A61K 45/06* | (2006.01) | |

(52) U.S. Cl.
CPC .............. *A61K 38/06* (2013.01); *A61K 38/07* (2013.01); *A61K 45/06* (2013.01)

(58) Field of Classification Search
CPC .............................. A61K 38/07; C07K 5/1019
See application file for complete search history.

(56) References Cited

U.S. PATENT DOCUMENTS

| | | | |
|---|---|---|---|
| 4,522,811 | A | 6/1985 | Eppstein et al. |
| 5,674,534 | A | 10/1997 | Zale et al. |
| 5,716,644 | A | 2/1998 | Zale et al. |
| 6,468,798 | B1 | 10/2002 | Debs et al. |
| 7,550,439 | B2 | 6/2009 | Szeto |
| 7,576,061 | B2 | 8/2009 | Szeto et al. |
| 7,718,620 | B2 | 5/2010 | Szeto et al. |
| 7,781,405 | B2 | 8/2010 | Szeto |
| 8,143,219 | B2 | 3/2012 | Szeto et al. |
| 8,404,646 | B2 | 3/2013 | Schiller et al. |
| 8,592,373 | B2 | 11/2013 | Szeto et al. |
| 8,618,061 | B2 | 12/2013 | Szeto |
| 8,940,696 | B2 | 1/2015 | Szeto et al. |
| 8,957,030 | B2 | 2/2015 | Szeto et al. |
| 9,241,933 | B2 | 1/2016 | Cohen et al. |
| 9,457,057 | B2 | 10/2016 | Tompkins et al. |
| 9,687,519 | B2 | 6/2017 | Wilson et al. |
| 10,047,395 | B2 | 8/2018 | Wilson |
| 10,793,597 | B2 | 10/2020 | Wilson |
| 11,083,771 | B2 | 8/2021 | Wilson et al. |
| 11,083,772 | B2 | 8/2021 | Wilson et al. |
| 11,312,993 | B2 | 4/2022 | Wilson |
| 11,771,734 | B2 * | 10/2023 | Wilson ................... A61K 38/07 514/21.9 |
| 2004/0248808 | A1 | 12/2004 | Szeto et al. |
| 2006/0084606 | A1 | 4/2006 | Szeto |
| 2006/0251641 | A1 | 11/2006 | Keimel |
| 2007/0015711 | A1 | 1/2007 | Szeto |
| 2007/0026090 | A1 | 2/2007 | Tirosh et al. |
| 2007/0027087 | A1 | 2/2007 | Szeto et al. |
| 2007/0135335 | A1 | 6/2007 | Collier et al. |
| 2007/0265216 | A1 | 11/2007 | Gross et al. |
| 2008/0318909 | A1 | 12/2008 | Sparagna et al. |
| 2009/0143279 | A1 | 6/2009 | Mootha et al. |
| 2009/0221514 | A1 | 9/2009 | Szeto et al. |
| 2009/0298848 | A1 | 12/2009 | Stewart |
| 2009/0305319 | A1 | 12/2009 | Baudenbacher et al. |
| 2010/0158995 | A1 | 6/2010 | Mill et al. |

(Continued)

FOREIGN PATENT DOCUMENTS

| | | | |
|---|---|---|---|
| CN | 1787831 | A | 6/2006 |
| CN | 1938042 | A | 3/2007 |

(Continued)

OTHER PUBLICATIONS

"The Voice of the Patient: Barth Syndrome" Presentation. Barth Syndrome Foundation, (2019).
Acín-Perez, et al., "Respiratory Active Mitochondrial Supercomplexes," Molecular Cell, Nov. 21, 2008, vol. 32, No. 4, pp. 529-539.
Aljabri, et al. "Lethal neonatal mitochondrial phenotype caused by a novel polymerase subunit gamma mutation," Medicine, vol. 97, No. 40(e12591) (2018) (pp. 1-7).

(Continued)

*Primary Examiner* — Jeanette M Lieb
(74) *Attorney, Agent, or Firm* — Foley & Lardner LLP

(57) ABSTRACT

The disclosure provides methods of preventing or treating Barth Syndrome in a mammalian subject, reducing risk factors associated with Barth Syndrome, and/or reducing the likelihood or severity of Barth Syndrome. The methods comprise administering to the subject an effective amount of an aromatic-cationic peptide to increase expression of TAZ1 in subjects in need thereof.

8 Claims, 5 Drawing Sheets

(56) References Cited

U.S. PATENT DOCUMENTS

| | | | |
|---|---|---|---|
| 2010/0190718 | A1 | 7/2010 | Schiller et al. |
| 2010/0311664 | A1 | 12/2010 | Szeto |
| 2010/0331265 | A1 | 12/2010 | Tompkins et al. |
| 2011/0008310 | A1 | 1/2011 | Cataldo et al. |
| 2011/0039766 | A1 | 2/2011 | Szeto |
| 2011/0082084 | A1 | 4/2011 | Szeto et al. |
| 2011/0136725 | A1 | 6/2011 | Dong |
| 2011/0172312 | A1 | 7/2011 | Miller et al. |
| 2011/0177047 | A1 | 7/2011 | Liu et al. |
| 2011/0197294 | A1 | 8/2011 | Gottlieb et al. |
| 2012/0021970 | A1 | 1/2012 | Schiller et al. |
| 2012/0046363 | A1 | 2/2012 | Stanley |
| 2012/0122957 | A1 | 5/2012 | Dillin et al. |
| 2013/0017150 | A1 | 1/2013 | Szeto et al. |
| 2013/0040901 | A1 | 2/2013 | Szeto et al. |
| 2013/0244957 | A1 | 9/2013 | Szeto et al. |
| 2013/0288985 | A1 | 10/2013 | Jurkunas |
| 2013/0345312 | A1 | 12/2013 | Jankowski et al. |
| 2014/0031432 | A1 | 1/2014 | Jankowski et al. |
| 2014/0107033 | A1 | 4/2014 | Szeto et al. |
| 2014/0288012 | A1 | 9/2014 | Tompkins et al. |
| 2014/0342004 | A1 | 11/2014 | Aprikyan et al. |
| 2014/0349941 | A1 | 11/2014 | Wilson et al. |
| 2014/0349942 | A1 | 11/2014 | Szeto |
| 2014/0378396 | A1 | 12/2014 | Wilson et al. |
| 2015/0010588 | A1 | 1/2015 | Szeto |
| 2015/0018288 | A1 | 1/2015 | Wilson et al. |
| 2015/0246092 | A1 | 9/2015 | Wilson et al. |
| 2015/0266946 | A1 | 9/2015 | Sinclair et al. |
| 2015/0353602 | A1 | 12/2015 | Szeto et al. |
| 2015/0359838 | A1 | 12/2015 | Szeto et al. |
| 2016/0175380 | A1 | 6/2016 | Jurkunas |
| 2016/0194708 | A1 | 7/2016 | Wilson |
| 2016/0228487 | A1 | 8/2016 | Wilson et al. |
| 2016/0361377 | A1 | 12/2016 | Wilson et al. |

FOREIGN PATENT DOCUMENTS

| | | |
|---|---|---|
| CN | 102711785 | 10/2012 |
| CN | 102784383 | 11/2012 |
| CN | 102834105 | 12/2012 |
| JP | 2013-521231 | 6/2013 |
| JP | 6918046 | 8/2021 |
| WO | WO-96/40073 A2 | 12/1996 |
| WO | WO-99/15154 A1 | 4/1999 |
| WO | WO-00/38651 A1 | 7/2000 |
| WO | WO-2004/070054 A2 | 8/2004 |
| WO | WO-2004/070054 A3 | 4/2005 |
| WO | WO-2005/072295 A2 | 8/2005 |
| WO | WO-2006/122140 | 11/2006 |
| WO | WO-2010/120431 A2 | 10/2010 |
| WO | WO-2011/044044 A1 | 4/2011 |
| WO | WO-2011/082084 A2 | 7/2011 |
| WO | WO-2011/082324 A1 | 7/2011 |
| WO | WO-2011/096398 A1 | 8/2011 |
| WO | WO-2011/106717 A1 | 9/2011 |
| WO | WO-2011/116007 A1 | 9/2011 |
| WO | WO-2011/139992 A1 | 11/2011 |
| WO | WO-2012/129427 | 9/2012 |
| WO | WO-2013/049697 | 4/2013 |
| WO | WO-2014/066419 | 5/2014 |

OTHER PUBLICATIONS

Amselem, et al., "A Large-Scale Method for the Preparation of Sterile and Nonpyrogenic Liposomal Formulations of Defined Size Distributions for Clinical Use." Liposome Technology, 1993, vol. 1, 2nd ed., CRC Press, pp. 502-525.

Aprikyan et al. "Advances in the understanding of Barth syndrome," British Journal of Haematology, vol. 161 (2013) (pp. 330-338).

Ashley, et al., "Depletion of mitochondrial DNA in fibroblast cultures from patients with POLG1 mutations is a consequence of catalytic mutations," Hum. Mol. Gene., 2008, vol. 17, No. 16, pp. 2496-2506.

Barth, et al. "An X-linked mitochondrial disease affecting cardiac muscle, skeletal muscle and neutrophil leucocytes," Journal of the Neurological Sciences, vol. 62 (1983) (pp. 327-355).

Birk et al. "The Mitochondrial-Targeted Compound SS-31 Re-Energizes Ischemic Mitochondria by Interacting with Cardiolipin," Journal of the American Society of Nephrology, vol. 24 (2013) (pp. 1250-1261).

Birk, et al., "Targeting cytochrome C for optimization of mitochondrial electron transport chain," FASEB Journal, 2011, vol. 25, No. 1, Abstract.

Blok, et al., "The unfolding clinical spectrum of POLG mutations," J. Med. Genet., 2009, vol. 46, No. 22, pp. 776-785.

CA Office Action on CA Patent Application No. 2916977 dated Mar. 8, 2022 (8 pages).

Calvani et al. "Mitochondrial pathways in sarcopenia of aging and disuse muscle atrophy," Biological Chemistry, vol. 394, No. 3 (2013) (pp. 393-414).

Chinnery, Patrick F. "Mitochondrial Disorders Overview" GeneReviews (2000).

Chonn, et al., "Recent Advances in Liposomal Drug-Delivery Systems," Curr. Opin. Biotechnol., Dec. 1995, vol. 6, Issue 6, pp. 698-708.

Colan, Steven D., "Classification of teh cardiomyopathies," Progress in Pediatric Cardiology, vol. 23, (2007) (pp. 5-15).

Communication pursuant to Article 94(3) EPC on EP Patent Application No. 19190165.1 dated Dec. 7, 2023 (7 pages).

Communication pursuant to Article 94(3) EPC on EP Patent Application No. 19190165.1 dated May 9, 2023 (8 pages).

Dai et al. "Cardiac Aging: From Molecular Mechanisms to Significance in Human Health and Disease," Antioxidants & Redox Signaling, vol. 16, No. 12 (2012) (pp. 1492-1526).

Dai et al. "Mitochondria and Cardiovascular Aging," Circulation Research, vol. 110 (2012) (pp. 1109-1124).

Dai et al. "Mitochondrial oxidative stress mediates Angiotension II-induced cardiac hypertrophy and Gaq overexpression-induced heart failure," Circulation Research, vol. 108, No. 7 (2011) (pp. 837-846).

Dai, et al., "Mitochondrial targeted antioxidant peptide ameliorates hypertensive cardiomyopathy," Journal of the American College of Cardiology, 2011, vol. 38, No. 1, pp. 73-82.

Decision of Reexamination on CN Patent Application No. 201480022764.9 dated Oct. 18, 2023 (12 pages) (with English Translation).

Decision of Rejection in CN Patent Application No. 201480022764.9 dated Mar. 19, 2019.

Decision of Rejection in CN Patent Application No. 201480022767.2 dated Sep. 18, 2018 (with English translation) (12 pages).

Diaz, et al., Cytochrome c Oxidase Is Required for the Assembly/Stability of Respiratory Complex I in Mouse Fibroblasts, Mol. Cell. Bio., Jul. 2006, vol. 26, No. 13, pp. 4872-4881.

EP Search Report dated Jul. 6, 2020.

Examination Report in EP Patent Application No. 14756991.7 mailed May 11, 2018.

Extended European Search Report on EP Patent Application No. 19190165.1 dated Feb. 5, 2020 (11 pages).

Extended Search Report in EP Patent Application 14757000 No. dated Jul. 16, 2016.

Extended Search Report in EP Patent Application No. 14756991.7 mailed Jul. 19, 2016.

Extended Search Report in EP Patent Application No. 19199765.9 dated May 6, 2020 (13 pages).

Farina, et al., "MR Findings in Leigh Syndrome with COX deficiency and SURF-1 Mutations," Am. J. Neuroradiol., 2002, vol. 23, pp. 1095-1100.

Ferraris, et al., "Progressive external ophthalmoplegia and vision and hearing loss in a patient with mutations in POLG2 and OPA1," Arch. Neurol., 2008, vol. 65, pp. 125-131.

Final Office Action in U.S. Appl. No. 14/771,411 dated Jan. 25, 2018.

Final Office Action on U.S. Appl. No. 14/771,411 Dtd Dec. 11, 2019.

Final Office Action on U.S. Appl. No. 15/626,255 dated Nov. 26, 2018, 13 pages.

(56) References Cited

OTHER PUBLICATIONS

Final Office Action on U.S. Appl. No. 16/101,078 dated Sep. 29, 2021 (7 pages).
Final Office Action on U.S. Appl. No. 16/930,028 dated Sep. 17, 2021 (22 pages).
Final Rejection in JP Application No. 2019-080101 dated Oct. 12, 2020 (with English translation) (7 pages).
Final Rejection in U.S. Appl. No. 15/626,255 dated Aug. 5, 2020.
Final Rejection in U.S. Appl. No. 16/929,370 dated Mar. 3, 2021 (7 pages).
Final Rejection on JP Patent Application No. 2019-133638 dated Apr. 4, 2022 (4 pages).
First Office Action in CN Application No. CN201910589605.1, Dated Nov. 2, 2022, with English-language translation.
Foreign Action other than Search Report on CA 2916977 Dtd May 15, 2020.
Foreign Action other than Search Report on EP 14757000.6 Dtd Sep. 25, 2018.
Foreign Action other than Search Report on EP 19199765.9 Dtd May 6, 2020.
Foreign Action other than Search Report on JP 2015-560380 Dtd Jun. 1, 2020.
Gregoriadis, "Engineering Liposomes for Drug Delivery: Progress and Problems," Trends in Biotechnology, Dec. 1995, vol. 13, No. 12, pp. 527-537.
Han, et al., "Shotgun lipidomics of cardiolipin molecular species in lipid extracts of biological samples," J Lipd Res, 2006, vol. 47, No. 4, pp. 864-879.
He, et al., "Abstract 15771: Mitochondria Targeted Antioxidant Prevents Mitochondrial Dysfunction Induced by Cardiolipin Deficiency," Circulation, Nov. 20, 2012, vol. 126, 2 pages.
Houtkooper, et al., "The Enigmatic Role of Tafazzin in Cardiolipin Metabolism," Biochimica et Biophysica Acta 1788, 2009, pp. 2003-2014.
Houtkooper, et al., "Cardiolipin and monolysocardiolipin analysis in fibroblasts, lymphocytes, and tissues using high-performance liquid chromatography-mass spectrometry as a diagnostic tests for Barth syndrome," Analytical Biochemistry, 2009, vol. 387, pp. 230-237.
International Search Report and Written Opinion in International Patent Application No. PCT/US14/19622 dated Jun. 3, 2014 (11 pages).
International Search Report and Written Opinion in International Patent Application No. PCT/US14/19645 dated Jun. 17, 2014 (11 pages).
International Search Report and Written Opinion in International Patent Application No. PCT/US14/43711 dated Jan. 2, 2015 (10 pages).
Jefferies, John L. "Barth Syndrome," American Journal of Medical Genetics Part C (Seminars in Medical Genetics), vol. 163C (2013) (pp. 198-205).
Jeffries, John Lynn. Letter to FDA.
Karkucinska-Wieckowska, et al., "Left Ventricular Noncompaction (LVNC) and Low Mitochondrial Membrane Potential are Specific for Barth Syndrome" J. Inherit. Metab. Dis., Jan. 2013, vol. 36, pp. 929-937.
Koshkin, et al., "Cardiolipin prevents rate-dependent uncoupling and provides osmotic stability in yeast mitochondria," Biochem. J., 2002, vol. 364, pp. 317-322.
Kozarich, et al., "Next generation therapeutics: Looking to the horizon: Editorial overview," Curr. Opin. Chem. Biol., 1998, vol. 2, Issue 4, pp. 439-440.
Lewis et al. "Biological Phenotypes of Heart Failure With Preserved Ejection Fraction," Journal of the American College of Cardiology, vol. 70, No. 17 (2017) (pp. 2186-2200).
Lichtenberg, et al., "Liposomes: Preparation, Characterization, and Preservation," Methods Biochem. Anal., 1998, vol. 33, pp. 337-462.
Liu, et al. "Novel cardiolipin therapeutic protects endothelial mitochondria during renal ischemia and mitigates microvascular rarefaction, inflammation, and fibrosis," American Journal of Physiology—Renal Physiology, vol. 306 (2014) (pp. F970-F980).
Ma, et al., "Superoxide Flashes: Early Mitochondrial Signals for Oxidative Stress-Induced Apoptosis" The Journal of Biological Chemistry, 2011, vol. 286, No. 31, pp. 27573-27581.
Ma, et al., "The Human TAZ Gene Complements Mitochondrial Dysfunction in the Yeast taz1? Mutant: Implications for Barth Syndrome," 2004, vol. 279, No. 43, pp. 44394-44399.
Makaryan, et al., "The Cellular and Molecular Mechanisms for Neutropenia in Barth Syndrome" European Journal of Haematology, 2011, vol. 88, pp. 195-209.
Martin, et al., "Leigh syndrome associated with mitochondrial complex I deficiency due to a novel mutation in the NDUFS1 gene," Arch. Neurol., 2005, vol. 62, pp. 659-661.
McHugh, et al., "Sensory ataxic neuropathy dysarthria and ophthalmoparesis (SANDO) in a sibling pair with a homozygous p.A467T POLG mutation," Muscle Nerve, 2010, vol. 41, No. 2, pp. 265-269.
Menezes, et al., "Peripheral neuropathy associated with mitochondrial disease in children," Dev. Med. & Child Neurol. 2012, vol. 54, pp. 407-414.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Moore et al. "Age-induced mitochondrial DNA point mutations are inadequate to alter metabolic homeostasis in response to nutrient challenge," Aging Cell, vol. 19 (2020) (pp. 1-18).
Non-Final Office Action in U.S. Appl. No. 14/771,408 dated Aug. 10, 2016.
Non-Final Office Action in U.S. Appl. No. 14/771,411 dated Apr. 27, 2017.
Non-Final Office Action in U.S. Appl. No. 14/771,411 dated Mar. 8, 2019, 15 pages.
Non-Final Office Action in U.S. Appl. No. 15/626,255 dated Apr. 6, 2021.
Non-Final Office Action in U.S. Appl. No. 15/626,255 dated Jan. 23, 2020.
Non-Final Office Action in U.S. Appl. No. 16/101,078 dated Mar. 24, 2021.
Non-Final Office Action in U.S. Appl. No. 16/929,370 dated Aug. 7, 2020.
Non-Final Office Action on U.S. Appl. No. 14/392,293 mailed Jun. 29, 2017.
Non-Final Office Action on U.S. Appl. No. 15/626,255 mailed Apr. 16, 2018.
Non-Final Rejection on U.S. Appl. No. 16/930,028 dated Feb. 25, 2021 (26 pages).
Notice of Allowance in U.S. Appl. No. 14/392,293 dated Apr. 12, 2018.
Notice of Allowance in U.S. Appl. No. 14/771,408 mailed Mar. 1, 2017.
Notice of Allowance in U.S. Appl. No. 14/771,411 dated Jun. 4, 2020.
Notice of Allowance in U.S. Appl. No. 14/771,411 dated May 28, 2020.
Notice of Allowance on U.S. Appl. No. 15/626,255 Dtd May 28, 2021.
Notice of Allowance on U.S. Appl. No. 16/101,078 dated Dec. 22, 2021.
Notice of Refusal in JP Patent Application No. 2015-560377 dated Sep. 3, 2018 (with English translation) (6 pages).
Notice of Refusal in JP Patent Application No. 2015-560380 dated Mar. 22, 2019 (with English translation) (6 pages).
Notification of Reexamination on CN Patent Application No. 201480022767.2 dated Sep. 1, 2022 (11 pages) (with English Translation).
Nurminen et al. "Pathogenicity in POLG syndromes: DNA polymerase gamma pathogenicity prediction server and database," BBA Clinical, vol. 7 (2017) (pp. 147-156).
Office Action in CA Patent Application No. 2916880 dated Jan. 6, 2020.
Office Action in CA Patent Application No. 2916977 dated May 27, 2020 (6 pages).

(56) References Cited

OTHER PUBLICATIONS

Office Action in CN Patent Application No. 201480022767.2 dated Mar. 28, 2017 (with English translation).
Office Action in CN Patent Application No. 201480022764.9 dated Jun. 17, 2017.
Office Action in CN Patent Application No. 201480022764.9 dated May 16, 2018.
Office Action in JP Patent Application No. 2015-560380 dated Dec. 25, 2017 (English translation not available).
Office Action in JP Patent Application No. 2015-560380 dated Jun. 1, 2020 (with English translation) (8 pages).
Office Action in JP Patent Application No. 2019-080101 dated Apr. 13, 2020 (with English translation) (7 pages).
Office Action in JP Patent Application No. 2019-133638 dated Aug. 3, 2020 (with English translation) (5 pages).
Office Action on CA Patent Application No. 2916977 dated Apr. 9, 2021.
Office Action on JP Patent Application No. 2019-133638 dated Jun. 3, 2021 (with English translation) (4 pages).
Office Action on JP Patent Application No. 2022-077425 dated May 28, 2023 (4 pages) (with English Translation).
Palsdottir, et al., "Lipids in membrane protein structures," Biochim Biophys Acta, Nov. 3, 2004, vol. 1666 (1-2), pp. 2-18.
Phoon et al., "Tafazzin knockdown in mice leads to a developmental cardiomyopathy with early diastolic dysfunction preceding myocardial noncompaction," J. Am Heart Assoc, Apr. 2012, vol. 1, No. 2, 13 pages.
Picard, Martin. "Assessment of mitochondrial function in skeletal muscle during disease, disuse and normal aging," Department of Kinesiology and Physical Education, McGill University, Montreal, Canada (2012).
Puccio et al. "Friedreich ataxia: a paradigm for mitochondrial diseases," Curr. Opin. Genetics Develop., 2002, vol. 12, pp. 272-277.
Raja et al. "Barth syndrome: A life-threatening disorder caused by abnormal cardiolipin remodeling," Journal of Rare Diseases Research & Treatment, vol. 2, No. 2 (2017) (pp. 58-62).
Reddy, "Controlled-Release, Pegylation, Liposomal Formulations: New Mechanisms in the Delivery of Injectable Drugs," Ann Pharmacother., 2000, vol. 34, pp. 915-923.
Restriction Requirement in U.S. Appl. No. 16/930,028 dated Nov. 19, 2020.
Restriction Requirement on U.S. Appl. No. 14/392,293, mailed Oct. 13, 2016.
Ristow et al., "Frataxin activates mitochondrial energy conversion and oxidative phosphorylation," PNAS, Oct. 24, 2000, vol. 97, No. 22, pp. 12239-12243.
Sabbah et al., "Acute Intravenous Infusion of Bendavia (MTP-131), A Novel Mitochondria-Targeting Peptide, Improves Left Ventricular Systolic Function in Dogs With Advanced Heart Failure", American Heart Association, Abstract.=, 2012.
Sabbah, Hani N. "Barth syndrome cardiomyopathy: targeting the mitochondria with elamipretide," Heart Failure Reviews (2020) (pp. 1-17).
Sabbah, Hani N. et al., "A canine model of chronic heart failure produced by multiple sequential coronary microembolizations," Am J Physiol.—Heart and Circulatory Physiology, 1991, vol. 260, Issue 4, pp. H1379-1384.
Saini-Chohan et al. "Cardiolipin biosynthesis and remodeling enzymes are altered during development of heart failure", Journal of Lipid Research vol. 50 (2008) (pp. 1600-1608).
Saneto, et al., "Aplers-Huttenlocher Syndrome," Pediatric Neurol., 2013, vol. 48, pp. 167-178.
Schlame, et al., "Barth syndrome, a human disorder of cardiolipin metabolism," FEBS Letters, 2006, vol. 580, pp. 5450-5455.
Schlame, et al., "The biosynthesis and functional role of cardiolipin," Progress in Lipid Research, 2000, vol. 39, pp. 257-288.
Schulte, et al., "Ataxia with Ophthalmoplegia or Sensory Neuropathy is Frequently caused by POLG Mutations," Neurology, Sep. 15, 2009, vol. 73, No. 11, pp. 898-900.

Second Office Action in CN Patent Application 201480022767.2, No. dated Nov. 9, 2017.
Shoemaker, et al. "Clinically Meaningful Change Estimates for the Six-Minute Walk Test and Daily Activity in Individuals With Chronic Heart Failure," Cardiopulmonary Physical Therapy Journal, vol. 24, No. 3 (2013) (pp. 21-29).
Siegel, et al., "Reversal of Age-Related Mitochondrial Dysfunction in vivo by Treatment with the Mitochondrially Targeted therapeutic SS-31," The FASEB Journal, Apr. 2012, vol. 26, No. 1, 1 page.
Spinazzola, et al., "Clinical and molecular features of mitochondrial DNA depletion syndromes," J. INhert. Metab. Dis., 2009, vol. 32, Issue 2, pp. 143-158.
Stewart, et al., "Novel POLG1 mutations associated with neuromuscular and liver phenotypes in adults and children," J. Med. Genet., Mar. 2009, vol. 46, No. 3, pp. 209-214.
Supplentary Tables. Elamipretide (MPT-131 for SC Injection) (2018).
Takeda, et al., "Barth syndrome diagnosed in the subclinical stage of heart failure based on the presence of lipid storage myopathy and isolated noncompaction of the ventricular myocardium," Eur J Pediatr, 2011, vol. 170, pp. 1481-1484.
Tarnavski, et al., "Mouse cardiac surgery: comprehensive techniques for the generation of mouse models of human diseases and their application for genomic studies," Physiol. Genomics, 2004, vol. 16, Issue 3, pp. 349-360.
The fact sheet of Ataxia Neuropathy Spectrum, retrieved from Genetics Home Reference website, published Feb. 26, 2019, 5 pages.
The fact sheet of Leigh Syndrome, retrieved from the Genetics Home Reference website, published Feb. 21, 2017, 8 pages.
The fact sheet of Progressive External Ophthalmoplegia, retrieved from Genetics Home Reference website, published Feb. 26, 2019, 7 pages.
The factsheet of Alpers Syndrome from the website of Genetic and Rare Disease Information Center at NIH. (rarediseases.info.nih.gov/diseases/5783/alpers-syndrome), retrieved on Sep. 13, 2021.
The Factsheet of ataxia-neuropathy-spectrum from the MedicinePlus website. (medlineplus.gov/download/genetics/condition/X ataxia-neuropathy-spectrum.pdf), (2020).
The Factsheet of Kearns-sayre-syndrome from the NIH website. (rarediseases. info. ni h.gov/diseases/6817 /kearns-sayre-syndrome), (2021).
The factsheet of POLG gene from MedicinePlus Website. (medlineplus.gov/download/genetics/gene/polg.pdf), (2020).
The factsheet of progressive external ophthalmoplegia (PEO) from the website of Genetic and Rare Disease Information Center at NIH. (rarediseases.info.nih.gov/diseases/4503/chronic-progressive-external-ophthalmoplegia), retrieved on Sep. 13, 2021.
The factsheet of sensory ataxia-neuropathy with dysarthria and ophthalmoparesis (SANDO) from the website of Genetic and Rare w Disease Information Center at NIH. (rarediseases.info.nih.gov/diseases/9998/sensory-ataxic-neuropathy-dysarthria-and-ophthalmoparesis), retrieved on Sep. 13. 2021.
Thompson, et al. "A phase 2/3 randomized clinical trial followed by an open-label extension to evaluate the effectiveness of elamipretide in Barth syndrome, a genetic disorder of mitochondrial cardiolipin metabolism," Genetics in Medicine, 2021, vol. 23(3), pp. 471-478.
Tiranti, et al., "Mutations of SURF-1 in Leigh Disease Associated with Cytochrome c Oxidase Deficiency," Am. J. Hum. Genet., Dec. 1998, vol. 63, No. 6, pp. 1609-1621.
US Notice of Allowance on U.S. Appl. No. 16/929,370 Dtd May 25, 2021.
US Office Action on U.S. Appl. No. 14/392,293 Dtd Oct. 13, 2016.
US Office Action on U.S. Appl. No. 16/929,370 Dtd Mar. 3, 2021.
Van Goethem, et al., "Mutation of POLG is associated with progressive external ophthalmoplegia characterized by mtDNA deletions," Nature Genetics, Jul. 2001, vol. 28, No. 3, pp. 211-212.
Voller, et al., "Enzyme immunoassays with special reference to ELISA techniques," J. Clinical Pathology, 1978, vol. 31, Issue 6, pp. 507-520.
Weiner, Alan L., Liposomes for Protein Delivery: Selecting Manufacture and Development Processes, Immunomethods, 1994, vol. 4, pp. 201-209.

(56) References Cited

OTHER PUBLICATIONS

Williams, et al., "Cytochrome c Oxidase Subassemblies in Fibroblast Cultures from Patients Carrying Mutations in COX10, SCO1, or SURF1," J. Biol. Chem., 2004, vol. 279, No. 9, pp. 7462-7469.

Wong, et al., "Molecular and Clinical Genetics of Mitochondrial Diseases Due to POLG Mutations," Hum. Mutat., Sep. 2008), vol. 29, No. 9, pp. E150-172.

Zhao et al., "Cell-permeable Peptide Antioxidants Targeted to Inner Mitochondrial Membrane inhibit Mitochondrial Swelling, Oxidative Cell Death, and Reperfusion Injury," The Journal of Biological Chemistry, Aug. 13, 2004, vol. 279, No. 33, pp. 34682-34690.

Zhao, et al., "Transcellular Transport of a Highly Polar 3+ Net Charge Opioid Tetrapeptide," Journal of Pharmacology and Experimental Therapeutics, 2003, vol. 304, No. 1, pp. 425-432.

Zhu, et al., "SURF1, encoding a factor involved in the biogenesis of cytochrome c oxidase, is mutated in Leigh syndrome," Nature Genetics, Dec. 1998, vol. 20, pp. 337-343.

Zou, et al., "An in vitro preliminary study of the radio-protective properties of antioxidant peptide SS31," Journal of Radiation Research and Radiation Proceeding, Oct. 2012, vol. 30, Edition 5, pp. 291-296, (English abstract only).

Communication pursuant to Article 94(3) EPC on EP Patent Application No. 19199765.9 dated Jan. 26, 2024 (4 pages).

Non-Final Office Action on U.S. Appl. No. 17/708,909 dated May 8, 2024.

Office Action in EP 19190165.1 dated Jun. 25, 2024.

Final Office Action on U.S. Appl. No. 17/708,909 Dtd Sep. 23, 2024.

Office Action on CA 2916977 dated Aug. 8, 2024.

U.S. Appl. No. 18/890,079, filed Sep. 19, 2024, Wilson, T.

NIH, "Ataxia neuropathy spectrum," 2021, Retrieved from medlineplus. gov/download/genetics/condition/ataxia-neuropathy-spectrum.pdf.

NIH, "POLG Gene," 2021, Mediline Plus, Retrieved from medlineplus. gov/download/genetics/gene/polg. pdf.

Non-Final Office Action on U.S. Appl. No. 17/963,697 Dtd Dec. 4, 2024.

* cited by examiner

METHODS AND COMPOSITIONS FOR THE PREVENTION OR TREATMENT OF BARTH SYNDROME

CROSS-REFERENCE TO RELATED PATENT APPLICATIONS

This application is continuation of U.S. application Ser. No. 17/371,475, filed Jul. 9, 2021, now U.S. Pat. No. 11,771,734, which is a continuation of U.S. application Ser. No. 16/929,370, filed Jul. 15, 2020, now U.S. Pat. No. 11,083,772, which is a continuation of U.S. application Ser. No. 15/626,255, filed Jun. 19, 2017, now U.S. Pat. No. 11,083,771, which is a continuation of U.S. application Ser. No. 14/771,408, filed Aug. 28, 2015, now U.S. Pat. No. 9,687,519, which is the U.S. 371 National Stage Application of International Application No. PCT/US2014/019622, filed Feb. 28, 2014, which claims priority to U.S. Provisional Application Nos. 61/771,534, filed Mar. 1, 2013, 61/771,642, filed Mar. 1, 2013, and 61/839,753, filed Jun. 26, 2013, all of which are incorporated herein by reference in their entirety.

TECHNICAL FIELD

The present technology relates generally to compositions and methods for preventing or treating Barth Syndrome, reducing risk factors associated with Barth Syndrome, and/or reducing the severity of Barth Syndrome. In particular, the present technology relates to administering an effective amount of an aromatic-cationic peptide to a subject in need thereof to normalize expression levels of TAZ1.

BACKGROUND

The following description is provided to assist the understanding of the reader. None of the information provided or references cited is admitted to be prior art to the present invention.

Barth Syndrome is a heritable disorder of phospholipid metabolism characterized by dilated cardiomyopathy (DCM), skeletal myopathy, neutropenia, growth delay and organic aciduria. The prevalence of Barth Syndrome is estimated at 1/454,000 live births, with an estimated incidence ranging from 1/400,000 to 1/140,000 depending on geographic location. Barth Syndrome is an X-linked disorder, and so disproportionately affects male patients.

Barth Syndrome is caused by mutations in the TAZ gene (tafazzin; Xq28), which encodes TAZ1, an acyltransferase involved in the metabolism of cardiolipin, a phospholipid localized to the inner mitochondrial membrane. Defective TAZ1 function results in abnormal remodeling of cardiolipin and compromises mitochondrial structure and respiratory chain function.

SUMMARY

In one aspect, the present disclosure provides a method for treating or preventing Barth Syndrome in a subject in need thereof, comprising administering to the subject a therapeutically effective amount of the peptide D-Arg-2'6'-Dmt-Lys-Phe-NH$_2$ or a pharmaceutically acceptable salt thereof.

In some embodiments, the subject displays reduced levels of TAZ1 expression compared to a normal control subject. In some embodiments, the peptide is administered daily for 6 weeks or more. In some embodiments, the peptide is administered daily for 12 weeks or more.

In some embodiments, the subject has been diagnosed as having Barth Syndrome. In some embodiments, the Barth Syndrome comprises one or more of cardiomyopathy, skeletal muscle abnormalities, neutropenia, slow development, weak muscle tone, increased levels of organic acids in the urine and blood, and frequent bacterial infections.

In some embodiments, the subject is human. In some embodiments, the peptide is administered orally, topically, systemically, intravenously, subcutaneously, intraperitoneally, or intramuscularly.

In some embodiments, the method further comprises separately, sequentially or simultaneously administering a cardiovascular agent to the subject. In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In some embodiments, the pharmaceutically acceptable salt comprises acetate or trifluoroacetate salt.

In one aspect, the present disclosure provides a method for increasing the expression of TAZ1 in a mammalian subject in need thereof, the method comprising: administering to the subject a therapeutically effective amount of the peptide D-Arg-2'6'-Dmt-Lys-Phe-NH$_2$ or a pharmaceutically acceptable salt thereof.

In some embodiments, the expression of TAZ1 in the subject is about 2-5 fold less than the level of TAZ1 expression in a normal control subject. In some embodiments, the peptide is administered daily for 6 weeks or more. In some embodiments, the peptide is administered daily for 12 weeks or more.

In some embodiments, the subject has been diagnosed has having, is suspected of having, or is at risk of having Barth Syndrome. In some embodiments, the Barth Syndrome comprises one or more of cardiomyopathy, skeletal muscle abnormalities, neutropenia, slow development, weak muscle tone, increased levels of organic acids in the urine and blood, and frequent bacterial infections.

In some embodiments, the subject is human. In some embodiments, the peptide is administered orally, topically, systemically, intravenously, subcutaneously, intraperitoneally, or intramuscularly.

In some embodiments, the method further comprises separately, sequentially or simultaneously administering a cardiovascular agent to the subject. In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxanc receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In some embodiments, the pharmaceutically acceptable salt comprises acetate or trifluoroacetate salt.

In one aspect, the present disclosure provides a method for reducing the risk of Barth Syndrome in a mammalian subject having decreased expression of TAZ1 compared to a normal control subject, the method comprising: administering to the subject a therapeutically effective amount of the peptide D-Arg-2'6'-Dmt-Lys-Phe-NH$_2$ or a pharmaceutically acceptable salt thereof.

In one aspect, the present disclosure provides a method for stabilizing cardiolipin remodeling in a mammalian subject having or suspected of having Barth Syndrome. In some embodiments, the mammalian subject has decreased expression of TAZ1 compared to a normal control subject. In some embodiments, the cardiolipin is 18:2 species of cardiolipin.

DETAILED DESCRIPTION

Figure 1:
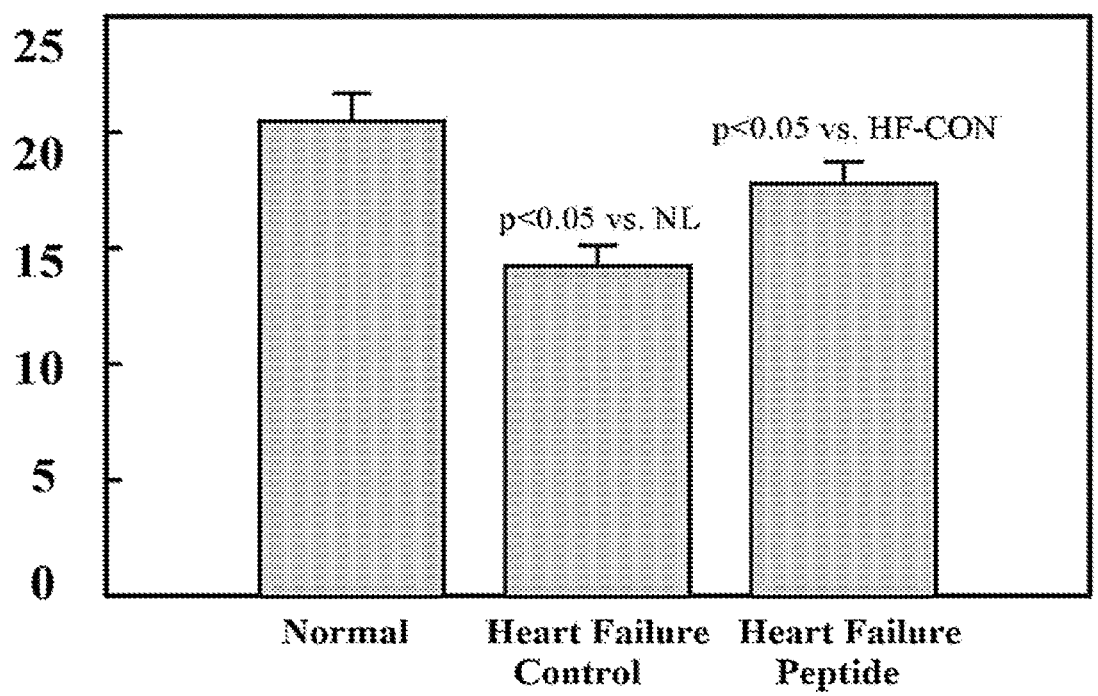
FIG. 1 is a chart showing the effects of D-Arg-2'6'-Dmt-Lys-Phe-NH$_2$ on levels of cardiolipin species 18:2-18:2-18:2-18:2 in a dog heart failure model.

It is to be appreciated that certain aspects, modes, embodiments, variations and features of the invention are described below in various levels of detail in order to provide a substantial understanding of the present invention. The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in an increase in (e.g., normalization of) the expression level of e.g., TAZ1 in a subject in need thereof. In the context of therapeutic or prophylactic applications, in some embodiments, the amount of a composition administered to the subject will depend on the type and severity of the disease and on the characteristics of the individual, such as general health, age, sex, body weight and tolerance to drugs. In some embodiments, it will also depend on the degree, severity and type of disease. The skilled artisan will be able to determine appropriate dosages depending on these and other factors. The compositions can also be administered in combination with one or more additional therapeutic compounds. In the methods described herein, aromatic-cationic peptides, such as D-Arg-2'6'-Dmt-Lys-Phe-NH$_2$, or a pharmaceutically acceptable salt thereof, such as acetate or trifluoroacetate salt, may be administered to a subject having one or more signs, symptoms, or risk factors of Barth Syndrome, such as, e.g., cardiomyopathy, skeletal muscle abnormalities, neutropenia, slow development, weak muscle tone, increased levels of organic acids in the urine and blood, and/or frequent bacterial infections, such as pneumonia. For example, a "therapeutically effective amount" of the aromatic-cationic peptides includes levels at which a subject's levels of TAZ1 expression are increased after administration, and/or at which the presence, frequency, or severity of one or more signs, symptoms, or risk factors of Barth Syndrome are reduced or eliminated. In some embodiments, a therapeutically effective amount reduces or ameliorates the physiological effects of a Barth Syndrome, and/or the risk factors of Barth Syndrome, and/or the likelihood of developing Barth Syndrome.

As used herein, the term "Barth Syndrome" refers to a heritable disorder of phospholipid metabolism caused by deficiencies of the TAZ1 acyltransferase. Signs and Symptoms of Barth Syndrome include, but are not limited to, cardiomyopathy, skeletal muscle abnormalities, neutropenia, slow development, weak muscle tone, increased levels of organic acids in the urine and blood, and/or frequent bacterial infections, such as pneumonia.

As used herein, the term "TAZ1" or "tafazzin" refers to the human X chromosome acyltransferase encoded by the TAZ gene. Illustrative sequences of TAZ1 isoforms are given by, for example, GenBank Accession Numbers NM 000116.3, NM_181311.2, NM_181312.2, and NM_181313.2.

As used herein, "isolated" or "purified" polypeptide or peptide refers to a polypeptide or peptide that is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, "normalizing" a subject's levels of TAZ1 expression refers to altering the subject's levels of TAZ1 expression in the direction of "normal" or wild-type expression levels. For example, normalizing TAZ1 expression levels in a subject with reduced TAZ1 expression compared to a normal subject refers to increasing the levels of TAZ1 expression. In some embodiments, normalizing TAZ1 expression in a subject refers to attenuating or reducing the degree of reduced TAZ1 expression compared to e.g., an untreated control subject.

As used herein "increasing" a subject's TAZ1 expression level means increasing the level of TAZ1 in the subject (e.g., a subject's TAZ1 expression level such as RNA and/or protein level) in an organ or tissue. In some embodiments, increasing TAZ1 expression level is an increase by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. Alternatively, or additionally, in some embodiments, increasing TAZ1 expression level is measured as an attenuation or reduction in the extent to which TAZ1 expression is decreased in a subject. In some embodiments, the TAZ1 reduction is decreased about 0.25 fold to about 0.5 fold, about 0.5 fold to about 0.75 fold, about 0.75 fold to about 1.0 fold, or about 1.0 fold to about 1.5 fold.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "treating" or "treatment" or "alleviation" refers to therapeutic treatment, wherein the object is to prevent, reduce, alleviate or slow down (lessen) the targeted pathologic condition or disorder. A subject is successfully "treated" for Barth Syndrome if, after receiving a therapeutic amount of the aromatic-cationic peptides, such as D-Arg-2'6'-Dmt-Lys-Phe-NH$_2$, or a pharmaceutically acceptable salt thereof, such as acetate or trifluoroacetate salt, according to the methods described herein, the subject shows observable and/or measurable reduction in or absence of one or more signs and symptoms of Barth Syndrome, such as, e.g., cardiomyopathy, skeletal muscle abnormalities, neutropenia, slow development, weak muscle tone, increased levels of organic acids in the urine and blood, and/or frequent bacterial infections, such as pneumonia. It is also to be appreciated that the various modes of treatment or prevention of medical conditions as described are intended to mean "substantial," which includes total but also less than total treatment or prevention, and wherein some biologically or medically relevant result is achieved. Treating Barth Syndrome, as used herein, also refers to treating reduced TAZ1 expression levels characteristic of the Syndrome, thereby causing an increase in TAZ1 expression compared to the subject's level of TAZ1 expression prior to treatment.

As used herein, "prevention" or "preventing" of a disorder or condition refers to a compound that, in a statistical sample, reduces the occurrence of symptoms of a disorder or condition in the treated sample relative to an untreated control sample, or delays the onset or reduces the severity of one or more symptoms of the disorder or condition relative to the untreated control sample. As used herein, preventing Barth Syndrome includes preventing or delaying the initiation of, preventing, delaying, or slowing the progression or advancement of, and/or reversing the progression of Barth Syndrome. As used herein, prevention of Barth Syndrome also includes preventing a recurrence of one or more signs or symptoms of Barth Syndrome.

Aromatic-Cationic Peptides

The present technology relates to methods and compositions for preventing or treating Barth Syndrome in a subject in need thereof. In some embodiments, the methods and compositions prevent one or more signs or symptoms of Barth Syndrome in a subject. In some embodiments, the methods and compositions increase the level of TAZ1 expression in a subject. In some embodiments, the methods and compositions reduce the likelihood that a subject with risk factors for Barth Syndrome will develop one or more signs or symptoms of Barth Syndrome.

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Tip), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta-, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \leq p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($2p_m \leq p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

| Aromatic groups and net positive charges ($3a \leq p_t + 1$ or $a = p_t = 1$) | | | | | | | | | | | | | | | | | | | |
|---|---|---|---|---|---|---|---|---|---|---|---|---|---|---|---|---|---|---|---|
| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

| Aromatic groups and net positive charges ($2a \leq p_t + 1$ or $a = p_t = 1$) | | | | | | | | | | | | | | | | | | | |
|---|---|---|---|---|---|---|---|---|---|---|---|---|---|---|---|---|---|---|---|
| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N, N-dimethylamido, N, N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 5

EXEMPLARY PEPTIDES

2',6'-Dmp-D-Arg-2',6'-Dmt-Lys-NH$_2$
2',6'-Dmp-D-Arg-Phe-Lys-NH$_2$
2',6'-Dmt-D-Arg-PheOrn-NH$_2$
2',6'-Dmt-D-Arg-Phe-Ahp(2-aminoheptanoicacid)-NH$_2$
2',6'-Dmt-D-Arg-Phe-Lys-NH$_2$
2',6'-Dmt-D-Cit-PheLys-NH$_2$
Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr-D-Phe-Lys-Phe
Asp-D-Trp-Lys-Tyr-D-His-Phe-Arg-D-Gly-Lys-NH$_2$
D-Arg-2',6'-Dmt-Lys-Phe-NH$_2$
D-Glu-Asp-Lys-D-Arg-D-His-Phe-Phe-D-Val-Tyr-Arg-Tyr-D-Tyr-Arg-His-Phe-NH$_2$
D-His-Glu-Lys-Tyr-D-Phe-Arg
D-His-Lys-Tyr-D-Phe-Glu-D-Asp-D-Asp-D-His-D-Lys-Arg-Trp-NH$_2$
D-Tyr-Trp-Lys-NH$_2$
Glu-Arg-D-Lys-Tyr-D-Val-Phe-D-His-Trp-Arg-D-Gly-Tyr-Arg-D-Met-NH$_2$
Gly-Ala-Lys-Phe-D-Lys-Glu-Arg-Tyr-His-D-Arg-D-Arg-Asp-Tyr-Trp-D-His-Trp-His-D-Lys-Asp.
Gly-D-Phe-Lys-His-D-Arg-Tyr-NH$_2$
His-Tyr-D-Arg-Trp-Lys-Phe-D-Asp-Ala-Arg-Cys-D-Tyr-His-Phe-D-Lys-Tyr-His-Ser-NH$_2$
Lys-D-Arg-Tyr-NH$_2$
Lys-D-Gln-Tyr-Arg-D-Phe-Trp-NH$_2$
Lys-Trp-D-Tyr-Arg-Asn-Phe-Tyr-D-His-NH$_2$
Met-Tyr-D-Arg-Phe-Arg-NH$_2$
Met-Tyr-D-Lys-Phe-Arg
Phe-Arg-D-His-Asp
Phe-D-Arg-2',6'-Dmt-Lys-NH$_2$
Phe-D-Arg-His
Phe-D-Arg-Lys-Trp-Tyr-D-Arg-His
Phe-D-Arg-Phe-Lys-NH$_2$
Phe-Phe-D-Tyr-Arg-Glu-Asp-D-Lys-Arg-D-Arg-His-Phe-NH$_2$
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$
Trp-D-Lys-Tyr-Arg-NH$_2$
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-NH$_2$
Tyr-D-Arg-Phe-Lys-NH$_2$
Tyr-D-His-Phe-D-Arg-Asp-Lys-D-Arg-His-Trp-D-His-Phe
Tyr-His-D-Gly-Met
Val-D-Lys-His-Tyr-D-Phe-Ser-Tyr-Arg-NH$_2$ In one embodiment, the peptides have mu-opioid receptor agonist activity (i.e., they activate the mu-opioid receptor). Peptides, which have mu-opioid receptor agonist activity, are typically those peptides that have a tyrosine residue or a tyrosine derivative at the N-terminus (i.e., the first amino acid position). Suitable derivatives of tyrosine include 2'-methyltyrosine (Mmt); 2', 6'-dimethyltyrosine (2'6'-Dmt); 3', 5'-dimethyltyrosine (3'5'Dmt); N, 2', 6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2', 6'-dimethyltyrosine to produce the compound having the formula 2', 6'-Dmt-D-Arg-Phe-Lys-NH$_2$. 2', 6'-Dmt-D-Arg-Phe-Lys-NH$_2$ has a molecular weight of 640 and carries a net three positive charge at physiological pH. 2', 6'-Dmt-D-Arg-Phe-Lys-NH$_2$ readily penetrates the plasma membrane of several mammalian cell types in an energy-independent manner (Zhao, et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2', 6'-dimethylphenylalanine (2', 6'-Dmp), N, 2', 6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2', 6'-dimethylphenylalanine (2'6'-Dmp). Tyr-D-Arg-Phe-Lys-NH$_2$ containing 2', 6'-dimethylphenylalanine at amino acid position 1 has the formula 2', 6'-Dmp-D-Arg-Phe-Lys-NH$_2$. In one embodiment, the amino acid sequence of 2', 6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and (e) Aromatic amino acids: Phe (F) Tyr(Y) Trp (W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | $NH_2$ |
| Tyr | D-Arg | Phe | Orn | $NH_2$ |
| Tyr | D-Arg | Phe | Dab | $NH_2$ |
| Tyr | D-Arg | Phe | Dap | $NH_2$ |
| 2'6'Dmt | D-Arg | Phe | Lys | $NH_2$ |
| 2'6'Dmt | D-Arg | Phe | Lys-NH(CH$_2$)$_2$-NH-dns | $NH_2$ |
| 2'6'Dmt | D-Arg | Phe | Lys-NH(CH$_2$)$_2$-NH-atn | $NH_2$ |
| 2'6'Dmt | D-Arg | Phe | dnsLys | $NH_2$ |
| 2'6'Dmt | D-Cit | Phe | Lys | $NH_2$ |
| 2'6'Dmt | D-Cit | Phe | Ahp | $NH_2$ |
| 2'6'Dmt | D-Arg | Phe | Orn | $NH_2$ |
| 2'6'Dmt | D-Arg | Phe | Dab | $NH_2$ |
| 2'6'Dmt | D-Arg | Phe | Dap | $NH_2$ |
| 2'6'Dmt | D-Arg | Phe | Ahp(2-aminoheptanoic acid) | $NH_2$ |
| Bio-2'6'Dmt | D-Arg | Phe | Lys | $NH_2$ |
| 3'5'Dmt | D-Arg | Phe | Lys | $NH_2$ |
| 3'5'Dmt | D-Arg | Phe | Orn | $NH_2$ |
| 3'5'Dmt | D-Arg | Phe | Dab | $NH_2$ |
| 3'5'Dmt | D-Arg | Phe | Dap | $NH_2$ |
| Tyr | D-Arg | Tyr | Lys | $NH_2$ |
| Tyr | D-Arg | Tyr | Orn | $NH_2$ |
| Tyr | D-Arg | Tyr | Dab | $NH_2$ |
| Tyr | D-Arg | Tyr | Dap | $NH_2$ |
| 2'6'Dmt | D-Arg | Tyr | Lys | $NH_2$ |
| 2'6'Dmt | D-Arg | Tyr | Orn | $NH_2$ |
| 2'6'Dmt | D-Arg | Tyr | Dab | $NH_2$ |
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| Tyr | D-Lys | Phe | Dap | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |
| 2'6'Dmt | D-Lys | Phe | Arg | $NH_2$ |
| 2'6'Dmt | D-Orn | Phe | Arg | $NH_2$ |
| 2'6'Dmt | D-Dab | Phe | Arg | $NH_2$ |
| 3'5'Dmt | D-Dap | Phe | Arg | $NH_2$ |
| 3'5'Dmt | D-Arg | Phe | Arg | $NH_2$ |
| 3'5'Dmt | D-Lys | Phe | Arg | $NH_2$ |
| 3'5'Dmt | D-Orn | Phe | Arg | $NH_2$ |
| Tyr | D-Lys | Tyr | Arg | $NH_2$ |
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2'6'Dmt | D-Arg | 2'6'Dmt | Arg | $NH_2$ |
| 2'6'Dmt | D-Lys | 2'6'Dmt | Arg | $NH_2$ |
| 2'6'Dmt | D-Orn | 2'6'Dmt | Arg | $NH_2$ |
| 2'6'Dmt | D-Dab | 2'6'Dmt | Arg | $NH_2$ |
| 3'5'Dmt | D-Dap | 3'5'Dmt | Arg | $NH_2$ |
| 3'5'Dmt | D-Arg | 3'5'Dmt | Arg | $NH_2$ |
| 3'5'Dmt | D-Lys | 3'5'Dmt | Arg | $NH_2$ |
| 3'5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N, 2',6'-trimethyttyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Tables 5-7 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc., New York (1997).

Cardiolipin Remodeling

Cardiolipin (cardiolipin) is an important component of the inner mitochondrial membrane, where it constitutes about 20% of the total lipid composition. In mammalian cells, cardiolipin is found almost exclusively in the inner mitochondrial membrane where it is essential for the optimal function of enzymes involved in mitochondrial metabolism.

Cardiolipin is a species of diphosphatidylglycerol lipid comprising two phosphatidylglycerols connected with a glycerol backbone to form a dimeric structure. It has four alkyl groups and potentially carries two negative charges. As there are four distinct alkyl chains in cardiolipin, the molecule has the potential for great complexity. However, in most animal tissues, cardiolipin contains 18-carbon fatty alkyl chains with 2 unsaturated bonds on each of them (18:2). It has been proposed that the 18:2 configuration is an important structural requirement for the high affinity of cardiolipin to inner membrane proteins in mammalian mitochondria. However, studies with isolated enzyme preparations indicate that its importance may vary depending on the protein examined.

Each of the two phosphates in cardiolipin can capture one proton. Although it has a symmetric structure, ionization of one phosphate happens at different levels of acidity than ionizing both, with pK1=3 and pK2>7.5. Hence, under normal physiological conditions (a pH of approximately 7.0), the molecule may carry only one negative charge. Hydroxyl groups (—OH and —O—) on the phosphate form stable intramolecular hydrogen bonds, forming a bicyclic resonance structure. This structure traps one proton, which is conducive to oxidative phosphorylation.

During the oxidative phosphorylation process catalyzed by Complex IV, large quantities of protons are transferred from one side of the membrane to another side causing a large pH change. Without wishing to be bound by theory, it has been suggested that cardiolipin functions as a proton trap within the mitochondrial membranes, strictly localizing the proton pool and minimizing pH in the mitochondrial intermembrane space. This function is thought to be due to the unique structure of cardiolipin, which, as described above, can trap a proton within the bicyclic structure while carrying a negative charge. Thus, cardiolipin can serve as an electron buffer pool to release or absorb protons to maintain the pH near the mitochondrial membranes.

In addition, cardiolipin has been shown to play a role in apoptosis. An early event in the apoptosis cascade involves cardiolipin. As discussed in more detail below, a cardiolipin-specific oxygenase produces cardiolipin-hydroperoxides which causes the lipid to undergo a conformational change. The oxidized cardiolipin then translocates from the inner mitochondrial membrane to the outer mitochondrial membrane where it is thought to form a pore through which cytochrome c is released into the cytosol. Cytochrome c can bind to the IP3 receptor stimulating calcium release, which further promotes the release of cytochrome c. When the cytoplasmic calcium concentration reaches a toxic level, the cell dies. In addition, extra-mitochondrial cytochrome c interacts with apoptotic activating factors, causing the formation of apoptosomal complexes and activation of the proteolytic caspase cascade.

Other roles proposed for cardiolipin are: 1) participation in stabilization of the physical properties of the membrane (Schlame, et al., 2000; Koshkin and Greenberg, 2002; Ma, et al., 2004), for example, membrane fluidity and osmotic stability and 2) participation in protein function via direct interaction with membrane proteins (Schlame, et al., 2000; Palsdottir and Hunte, 2004). Cardiolipin has been found in tight association with inner membrane protein complexes such as the cytochrome bc1 complex (complex III). As well, it has been localized to the contact sites of dimeric cytochrome c oxidase, and cardiolipin binding sites have also been found in the ADP/ATP carrier (AAC; for review see Palsdottir and Hunte, 2004). Recent work also suggests a role of cardiolipin in formation of respiratory chain supercomplexes (respirasomes).

The major tetra-acyl molecular species are 18:2 in each of the four fatty acyl positions of the cardiolipin molecule (referred to as the 18:2-18:2-18:2-18:2 cardiolipin species). Remodeling of cardiolipin is essential to obtain this enrichment of cardiolipin with linoleate because cardiolipin synthase has no molecular species substrate specificity for cytidine-5'-diphosphate-1,2-diacyl-sn-glycerol. In addition, the species pattern of cardiolipin precursors is similar enough to imply that the enzymes of the cardiolipin synthetic pathway are not molecular species-selective. Alterations in the molecular composition of cardiolipin are associated with various disease states.

Remodeling of cardiolipin occurs via at least three enzymes. Mitochondrial cardiolipin is remodeled by a deacylation-reacylation cycle in which newly synthesized cardiolipin was rapidly deacylated to monolysocardiolipin (MLCL) and then reacylated back to cardiolipin. MLCL AT1 is responsible for the deacylation and ALCAT1 is responsible for the reacylation. In addition to these mitochondrial and microsomal acyltransferase activities, mitochondrial cardiolipin may be remodeled by a mitochondrial cardiolipin transacylase. Tafazzin (TAZ1) is a cardiolipin transacylase that specifically remodels mitochondrial cardiolipin with linoleic acid.

Barth Syndrome

Barth Syndrome is a heritable disorder of phospholipid metabolism characterized by dilated cardiomyopathy (DCM), skeletal myopathy, neutropenia, growth delay and organic aciduria. The prevalence of Barth Syndrome is estimated at 1/454,000 live births, with an estimated incidence ranging from 1/400,000 to 1/140,000 depending on geographic location. Barth Syndrome is an X-linked disorder, and so disproportionately affects male patients.

Barth Syndrome is caused by mutations in the TAZ gene (tafazzin; Xq28), which encodes TAZ1, an acyltransferase involved in the metabolism of cardiolipin, a phospholipid localized to the inner mitochondrial membrane. Defective TAZ1 function results in abnormal remodeling of cardiolipin and compromises mitochondrial structure and respiratory chain function. TAZ1 is expressed at high levels in cardiac and skeletal muscle and is involved in the maintenance of the inner membrane of mitochondria. TAZ1 is involved in maintaining levels of cardiolipin, which is essential for energy production in the mitochondria.

Clinical presentation of Barth Syndrome is highly variable. Most subjects develop DCM during the first decade of life, and typically during the first year of life, which may be accompanied by endocardial fibroelastosis (EFE) and/or left ventricular noncompaction (LVNC). The manifestations of Barth Syndrome may begin in utero, causing cardiac failure, fetal hydrops and miscarriage or stillbirth during the 2nd/3rd trimester of pregnancy. Ventricular arrhythmia, especially during adolescence, can lead to sudden cardiac death. There is a significant risk of stroke. Skeletal (mostly proximal) myopathy causes delayed motor milestones, hypotonia, severe lethargy or exercise intolerance, here is a tendency to hypoglycemia during the neonatal period. Ninety percent of patients show mild to severe intermittent or persistent neutropenia with a risk of septicemia, severe bacterial sepsis, mouth ulcers and painful gums. Lactic acidosis and mild anemia may occur. Affected boys usually show delayed puberty and growth delay that is observed until the late teens or early twenties, when a substantial growth spurt often occurs. Patients may also present severe difficulties with adequate food intake. Episodic diarrhea is common. Many patients have a similar facial appearance with chubby cheeks, deep-set eyes and prominent ears.

In some embodiments, treatment with an aromatic-cationic peptide, such as D-Arg-2'6'-Dmt-Lys-Phe-NH$_2$, or a pharmaceutically acceptable salt thereof, such as acetate or trifluoroacetate salt, increases the expression of TAZ1 in a tissue or an organ in mammalian subjects that have suffered or are at risk of suffering Barth Syndrome. By way of example, but not by way of limitation, in some embodiments, the level of TAZ1 expression is increased in the myocardium of a subject in need thereof.

In some embodiments, increasing TAZ1 expression level is measured as a attenuation or reduction in the extent to which TAZ1 expression is decreased in a subject. In some embodiments, the TAZ1 reduction is decreased about 0.25 fold to about 0.5 fold, about 0.5 fold to about 0.75 fold, about 0.75 fold to about 1.0 fold, or about 1.0 fold to about 1.5 fold.

Therapeutic Methods

The following discussion is presented by way of example only, and is not intended to be limiting.

It is to be understood that increasing the expression level of TAZ1 in a subject in need thereof (e.g., RNA and/or protein level) will reduce the risk, severity, presentation/onset of any number of negative physical effects. One aspect of the present technology includes methods of treating reduced TAZ1 expression in a subject diagnosed as having, suspected as having, or at risk of having reduced TAZ1 expression levels. One aspect of the present technology includes methods of treating Barth Syndrome in a subject diagnosed as having, suspected as having, or at risk of having Barth Syndrome. In therapeutic applications, compositions or medicaments are administered to a subject suspected of, or already suffering from such a disease, such as, e.g., decreased TAZ1 expression levels or Barth Syndrome, in an amount sufficient to cure, or at least partially arrest, the symptoms of the disease, including its complications and intermediate pathological phenotypes in development of the disease.

Subjects suffering from decreased TAZ1 expression levels or Barth Syndrome can be identified by any or a combination of diagnostic or prognostic assays known in the art. For example, typical symptoms of Barth Syndrome include symptoms such as, e.g., cardiomyopathy, skeletal muscle abnormalities, neutropenia, slow development, weak muscle tone, increased levels of organic acids in the urine and blood, and/or frequent bacterial infections, such as pneumonia. In some embodiments, the subject may exhibit reduced levels of TAZ1 expression compared to a normal subject, which is measureable using techniques known in the art. In some embodiments, the subject may exhibit one or more mutations in the TAZ gene associated with Barth Syndrome, which are detectable using techniques known in the art.

Prophylactic Methods

In one aspect, the present technology provides a method for preventing or delaying the onset of Barth Syndrome or symptoms of Barth Syndrome in a subject at risk of having reduced levels of TAZ1 expression compared to a normal subject. In some embodiments, the subject may exhibit one or more mutations in the TAZ gene associated with Barth Syndrome, which are detectable using techniques known in the art. Subjects at risk for reduced TAZ1 expression levels or Barth Syndrome can be identified by, e.g., any or a combination of diagnostic or prognostic assays known in the art. In prophylactic applications, pharmaceutical compositions or medicaments of aromatic-cationic peptides, such as D-Arg-2'6'-Dmt-Lys-Phe-NH$_2$, or a pharmaceutically acceptable salt thereof, such as acetate or trifluoroacetate salt, are administered to a subject susceptible to, or otherwise at risk of a disease or condition such as e.g., Barth Syndrome, in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the disease or disorder, such that symptoms of the disease or disorder is prevented or, alternatively, delayed in its progression.

Subjects or at risk for reduced TAZ1 expression levels or Barth Syndrome may exhibit one or more of the following non-limiting risk factors: cardiomyopathy, skeletal muscle abnormalities, neutropenia, slow development, weak muscle tone, increased levels of organic acids in the urine and blood, and/or frequent bacterial infections, such as pneumonia.

Determination of the Biological Effect of the Aromatic-Cationic Peptide-Based Therapeutic In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect increasing TAZ1 expression, and preventing or treating Barth Syndrome. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of D-Arg-2'6'-Dmt-Lys-Phe-NH$_2$, or a pharmaceutically acceptable salt thereof, such as acetate or trifluoroacetate salt.

Heart failure has been induced in different species with volume overload, pressure overload, fast pacing, myocardial ischemia, cardiotoxic drugs, or genetically modified models. Hypertension is associated with an increased risk for the development of heart failure. In one mouse model, angiotensin II (Ang II) increases blood pressure and induces cardiomyocyte hypertrophy, increased cardiac fibrosis, and impaired cardiomyocyte relaxation. Infusion of angiotensin to mice by mini osmotic pump increases systolic and diastolic blood pressure, increases heart weight and left ventricular thickness (LVMI), and impaired myocardial performance index (MPI). TAZ1 expression levels are monitored at various time points before, during and after heart failure induction.

In a second illustrative mouse model, sustained high level expression of Gaq can lead to marked myocyte apoptosis, resulting in cardiac hypertrophy and Heart failure by 16 weeks of age (D'Angelo, et al., 1998). The β-adrenergic receptors (βARs) are primarily coupled to the heterotrimeric G protein, Gs, to stimulate adenylyl cyclase activity. This association generates intracellular cAMP and protein kinase A activation, which regulate cardiac contractility and heart rate. Overexpression of Gaq leads to decreased responsiveness to β-adrenergic agonists and results in heart failure. TAZ1 expression levels are monitored at various time points before, during and after heart failure induction.

Experimental constriction of the aorta by surgical ligation is also widely used as a model of heart failure. Transaortic constriction (TAC) results in pressure overload induced heart failure, with increase in left ventricular (LV) mass. TAC is performed as described by Tamayski O, et al. (2004) using a 7-0 silk double-knot suture to constrict the ascending aorta. After TAC, mice develop heart failure within a period of 4 weeks. TAZ1 expression levels are monitored at various time points before, during and after heart failure induction.

Modes of Administration and Effective Dosages

Any method known to those in the art for contacting a cell, organ or tissue with an aromatic-cationic peptide of the present technology, such as D-Arg-2'6'-Dmt-Lys-Phe-NH$_2$, or a pharmaceutically acceptable salt thereof, such as acetate or trifluoroacetate salt, may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides, such as D-Arg-2'6'-Dmt-Lys-Phe-NH$_2$, or a pharmaceutically acceptable salt thereof, such as acetate or trifluoroacetate salt, are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate or trifluoroacetate salt.

The aromatic-cationic peptides described herein, such as D-Arg-2'6'-Dmt-Lys-Phe-NH$_2$, or a pharmaceutically acceptable salt thereof, such as acetate or trifluoroacetate salt, can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. One skilled in the art would appreciate, there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immnunomethods*, 4(3):201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100:63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The subject treated in accordance with present methods can be any mammal or animal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In some embodiments, the aromatic-cationic peptides, such as D-Arg-2'6'-Dmt-Lys-Phe-NH$_2$, or a pharmaceutically acceptable salt thereof, such as acetate or trifluoroacetate salt, may be combined with one or more additional agents for the prevention or treatment of reduced TAZ1 expression levels or Barth Syndrome. Drug treatment for reduced TAZ1 expression levels or Barth Syndrome typically involves antibiotics, granulocyte colony stimulating factor (GCSF), and agents for the control of cardiac conditions, including but not limited to, for example, diuretics, ACE inhibitors, digoxin (digitalis), calcium channel blockers, and beta-blockers. In mild cases, thiazide diuretics, such as hydrochlorothiazide at 25-50 mg/day or chlorothiazide at 250-500 mg/day, are useful. However, supplemental potassium chloride may be needed, since chronic diuresis causes hypokalemis alkalosis. Moreover, thiazide diuretics usually are not effective in patients with advanced symptoms of Barth Syndrome. Typical doses of ACE inhibitors include captopril at 25-50 mg/day and quinapril at 10 mg/day.

In one embodiment, the aromatic-cationic peptide, such as D-Arg-2'6'-Dmt-Lys-Phe-NH$_2$, or a pharmaceutically acceptable salt thereof, such as acetate or trifluoroacetate salt, is combined with an adrenergic beta-2 agonist. An "adrenergic beta-2 agonist" refers to adrenergic beta-2 agonists and analogues and derivatives thereof, including, for example, natural or synthetic functional variants, which have adrenergic beta-2 agonist biological activity, as well as fragments of an adrenergic beta-2 agonist having adrenergic beta-2 agonist biological activity. The term "adrenergic beta-2 agonist biological activity" refers to activity that mimics the effects of adrenaline and noradrenaline in a subject and which improves myocardial contractility in a patient having Barth Syndrome. Commonly known adrenergic beta-2 agonists include, but are not limited to, clenbuterol, albuterol, formeoterol, levalbuterol, metaproterenol, pirbuterol, salmeterol, and terbutaline.

In one embodiment, the aromatic-cationic peptide, such as D-Arg-2'6'-Dmt-Lys-Phe-NH$_2$, or a pharmaceutically acceptable salt thereof, such as acetate or trifluoroacetate salt, is combined with an adrenergic beta-1 antagonist. Adrenergic beta-1 antagonists and adrenergic beta-1 blockers refer to adrenergic beta-1 antagonists and analogues and derivatives thereof, including, for example, natural or synthetic functional variants which have adrenergic beta-1 antagonist biological activity, as well as fragments of an adrenergic beta-1 antagonist having adrenergic beta-1 antagonist biological activity. Adrenergic beta-1 antagonist biological activity refers to activity that blocks the effects of adrenaline on beta receptors. Commonly known adrenergic beta-1 antagonists include, but are not limited to, acebutolol, atenolol, betaxolol, bisoprolol, esmolol, and metoprolol.

Clenbuterol, for example, is available under numerous brand names including Spiropent® (Boehinger Ingelheim), Broncodil® (Von Boch 1), Broncoterol® (Quimedical PT), Cesbron® (Fidelis PT), and Clenbuter® (Biomedica Foscama). Similarly, methods of preparing adrenergic beta-1 antagonists such as metoprolol and their analogues and derivatives are well-known in the art. Metoprolol, in particular, is commercially available under the brand names Lopressor® (metoprolol tartate) manufactured by Novartis Pharmaceuticals Corporation, One Health Plaza, East Hanover, N.J. 07936-1080. Generic versions of Lopressor® are also available from Mylan Laboratories Inc., 1500 Corporate Drive, Suite 400, Canonsburg, Pa. 15317; and Watson Pharmaceuticals, Inc., 360 Mt. Kemble Ave. Morristown, N.J. 07962. Metoprolol is also commercially available under the brand name Toprol XL®, manufactured by Astra Zeneca, LP.

In one embodiment, an additional therapeutic agent is administered to a subject in combination with an aromatic cationic peptide, such that a synergistic therapeutic effect is produced. Therefore, lower doses of one or both of the therapeutic agents may be used in treating Barth Syndrome, resulting in increased therapeutic efficacy and decreased side-effects.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present invention is further illustrated by the following examples, which should not be construed as limiting in any way.

Example 1—Effects of Aromatic-Cationic Peptides on Heart Mitochondrial Cardiolipin in a Dog Model of Heart Failure This example demonstrates the effect of the aromatic-cationic peptide D-Arg-2'6'-Dmt-Lys-Phe-NH$_2$ on levels of heart mitochondrial cardiolipin in dogs with coronary microembolization-induced heart failure. In particular, the effects of D-Arg-2'6'-Dmt-Lys-Phe-NH$_2$ on levels of the 18:2-18:2-18:2-18:2 cardiolipin species are evaluated.

Methods

Heart failure was induced in dogs via multiple sequential intracoronary microembolizations as described in Sabbah, et al., *Am J Physiol*. (1991) 260:H1379-84, herein incorporated by reference in its entirety. Half the dogs were subsequently treated with the mitochondrial peptide; the other half were treated with drug vehicle and served as controls. Peptide treatment was started upon induction of heart failure (HF), defined as left ventricular ejection fraction of approximately 30%. The daily dose of the peptide was 0.5 mg/kg/day administered intravenously. At the end of the treatment phase (12 weeks) dogs in both the vehicle and treatment groups were sacrificed and a sample of heart muscle from the left ventricle was removed, washed with saline, and immediately frozen and stored at −80° C. For cardiolipin analysis, lipids were extracted from the heart tissue sample with a chloroform/methanol solution (Bligh Dyer extraction). Individual lipid extracts were reconstituted with chloroform:methanol (1:1), flushed with $N_2$, and then stored at −20° C. before analysis via electrospray ionization mass spectroscopy using a triple-quadrupole mass spectrometer equipped with an automated nanospray apparatus. Enhanced multidimensional mass spectrometry-based shotgun lipidomics for cardiolipin was performed as described by Han, et al., "*Shotgun lipidomics of cardiolipin molecular species in lipid extracts of biological samples,*" *J Lipid Res* 47(4)864-879 (2006).

Results

The 18:2 cardiolipin species was significantly reduced in untreated heart failure dogs (Heart Failure, Control) (p<0.05) as compared to cardiac tissue from normal subjects (Normal). FIG. 1. However, heart failure dogs treated with D-Arg-2'6'-Dmt-Lys-Phe-NH$_2$ (Heart Failure, Peptide) had levels of 18:2 cardiolipin that were similar to normal subjects, and greater than the heart failure control subjects (p<0.05). FIG. 1.

Conclusions

The 18:2 cardiolipin species is reduced in heart failure subjects. The reduction of 18:2 cardiolipin leads to poor oxidative phosphorylation and subsequent LV dysfunction. Chronic treatment with D-Arg-2'6'-Dmt-Lys-Phe-NH$_2$ normalized 18:2 cardiolipin, which leads to improved LV function and rate of mitochondrial ATP synthesis.

These results show that aromatic-cationic peptides of the present invention, such as D-Arg-2'6'-Dmt-Lys-Phe-NH$_2$, or a pharmaceutically acceptable salt thereof, such as acetate or trifluoroacetate salt, are useful in the prevention and treatment of diseases and conditions associated with aberrant cardiolipin levels. In particular, these results show that aromatic-cationic peptides of the present invention, such as D-Arg-2'6'-Dmt-Lys-Phe-NH$_2$, or a pharmaceutically acceptable salt thereof, such as acetate or trifluoroacetate salt, are useful in methods comprising administration of the peptide to subjects in need of normalization of cardiolipin levels and remodeling.

Example 2—Effects of Aromatic-Cationic Peptides on TAZ1 Expression in a Dog Model of Heart Failure This example demonstrates the effect of the aromatic-cationic peptide D-Arg-2'6'-Dmt-Lys-Phe-NH$_2$ on levels of TAZ1 expression in dogs with coronary microembolization-induced heart failure. In particular, the effects of D-Arg-2'6'-Dmt-Lys-Phe-NH$_2$ on levels of TAZ1 mRNA are evaluated.

Methods

Twelve dogs were subject to coronary microembolization-induced heart failure (LV ejection fraction ~30%) as described above in Example 1. Subjects were randomized into D-Arg-2'6'-Dmt-Lys-Phe-NH$_2$-treated and control groups for a three-month trial. Subjects received subcutaneous injections of D-Arg-2'6'-Dmt-Lys-Phe-NH$_2$ (0.5 mg/kg once daily, n=6) or saline (Untreated-HF Control, n=6). RNA was prepared from LV tissue of all subjects at the end of the treatment phase and from the LV of six normal subject controls. Levels of TAZ1 mRNA were determined by real-time PCR. Changes in mRNA levels were expressed as fold reduction using the CT Method, with normalization to a glyceraldehyde 1,3 diphosphate dehydrogenase (GAPDH) internal control.

Results

Figure 2:
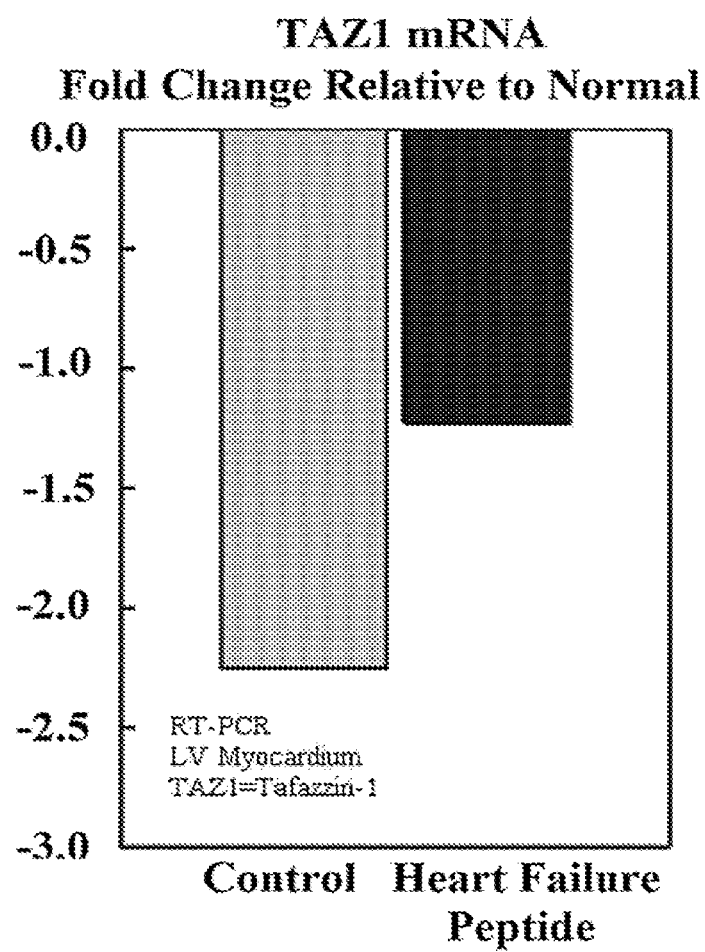
FIG. 2 is a chart showing the effects of D-Arg-2'6'-Dmt-Lys-Phe-NH$_2$ on levels of TAZ1 expression in a dog heart failure model.

Levels of TAZ1 mRNA were reduced 2.25-fold in heart failure subjects receiving saline control as compared to normal subjects. FIG. 2. Treatment with D-Arg-2'6'-Dmt-Lys-Phe-NH$_2$ attenuated the decrease in TAZ1 to only 1.23-fold, relative to normal subjects. FIG. 2.

Conclusions

Heart failure is associated with dysregulation of cardiolipin remodeling enzymes that can lead to pathologic remodeling of cardiolipin and to structural and functional mitochondrial abnormalities. Chronic therapy with D-Arg-2'6'-Dmt-Lys-Phe-NH$_2$ partially reverses these maladaptations thus allowing for resumption of physiologic post-biosynthesis remodeling of cardiolipin.

These results show that aromatic-cationic peptides of the present invention, such as D-Arg-2'6'-Dmt-Lys-Phe-NH$_2$, or a pharmaceutically acceptable salt thereof, such as acetate or trifluoroacetate salt, are useful in the prevention and treatment of diseases and conditions associated with reduced TAZ1 expression levels. In particular, these results show that aromatic-cationic peptides of the present invention, such as D-Arg-2'6'-Dmt-Lys-Phe-NH$_2$, or a pharmaceutically acceptable salt thereof, such as acetate or trifluoroacetate salt, are useful in methods comprising administration of the peptide to subjects in need of normalization of TAZ1 expression levels, such as, for example, subjects having Barth Syndrome.

Example 3—Effects of Aromatic Cationic Peptides on Mitochondrial Ultrastructure and Organization This example demonstrates that aromatic-cationic peptides, such as D-Arg-2'6'-Dmt-Lys-Phe-NH$_2$, or a pharmaceutically acceptable salt thereof, such as acetate or trifluoroacetate salt, are useful in the treatment of Barth Syndrome.

Figure 3:
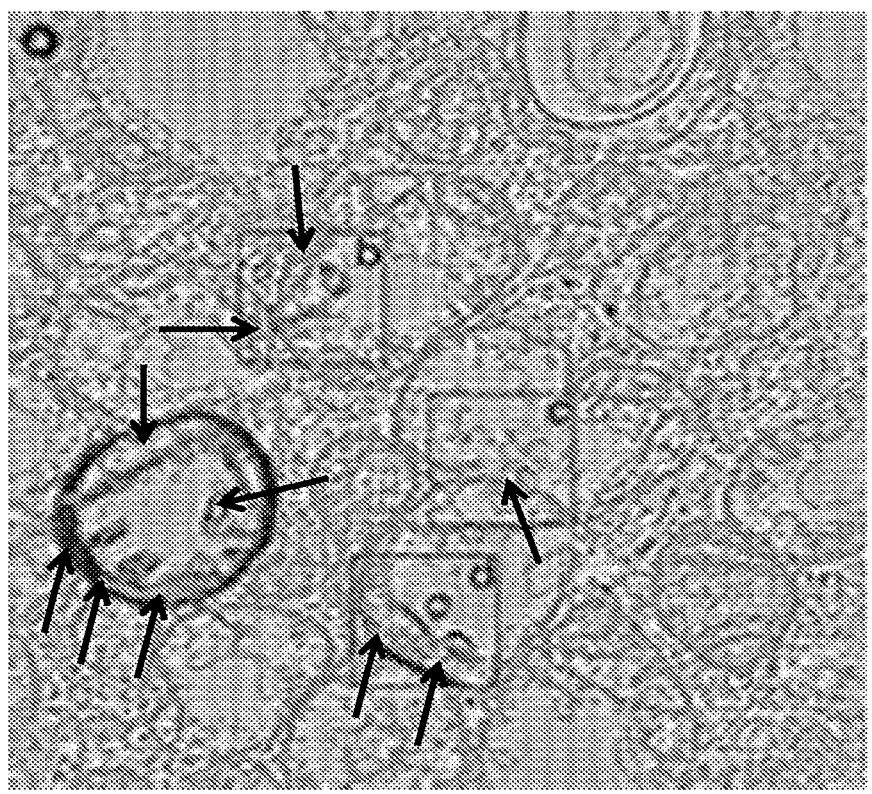
FIG. 3 is an electron microscopy image of mitochondria in a Barth Syndrome patient.

A tissue sample from a subject with Barth Syndrome and tissue samples from a subject with cardiac disease was prepared for electron microscopy imaging of the mitochondria using standards known in the art. The tissue sample from the Barth Syndrome subject was stained and showed abnormal features or structures within the mitochondria's ultrastructure and organization (see arrows in FIG. 3), some of which are highlighted in boxes b-d. FIG. 3.

Figure 4A:
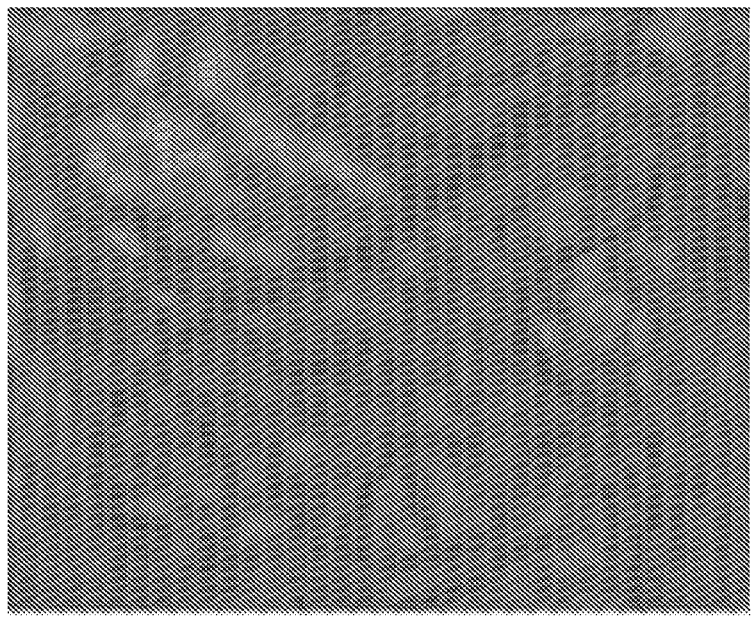
FIG. 4A is an electron microscopy image of the ultrastructure of mitochondria in cardiac disease.
Figure 4B:
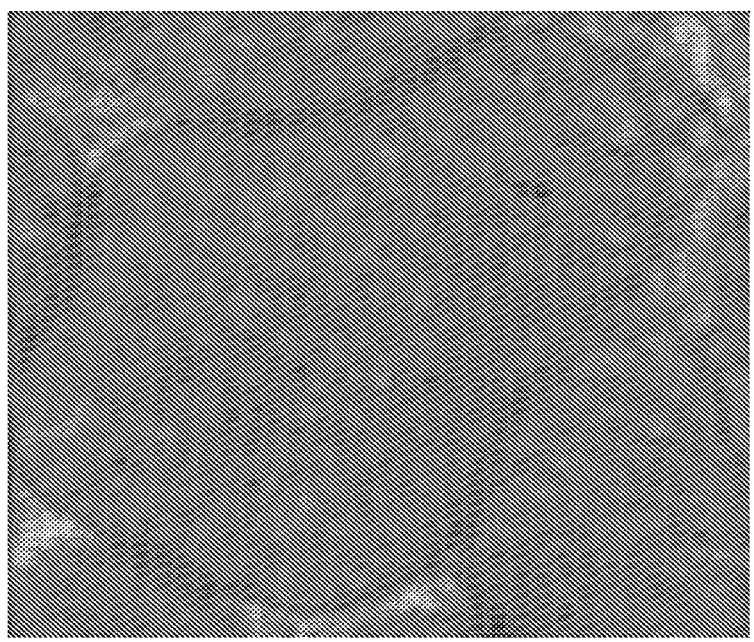
FIG. 4B is an electron microscopy image of the ultrastructure of mitochondria in cardiac disease treated with D-Arg-2'6'-Dmt-Lys-Phe-NH$_2$.

Similar derangement of mitochondrial ultrastructure was seen in the tissue sample from a cardiac disease subject. FIG. 4A. Treating a cardiac disease subject with an effective amount of D-Arg-2'6'-Dmt-Lys-Phe-NH$_2$ ameliorated the abnormal features of the ultrastructure of the mitochondria. FIG. 4B.

Figure 5A:
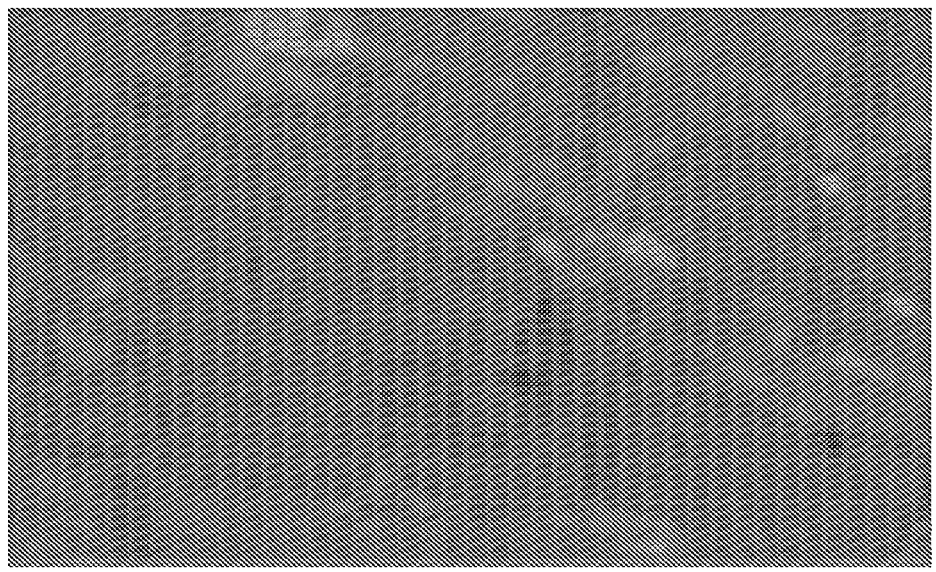
FIG. 5A is an electron microscopy image of the organization of mitochondria in cardiac disease.
Figure 5B:
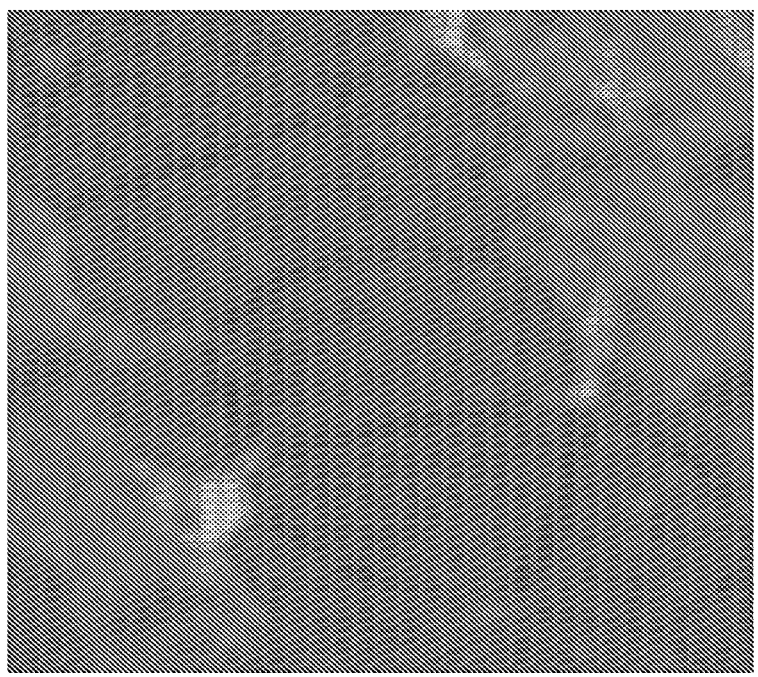
FIG. 5B is an electron microscopy image of the organization of mitochondria in cardiac disease treated with D-Arg-2'6'-Dmt-Lys-Phe-NH$_2$.

Furthermore, the amelioration of the pathological effects of cardiac disease in mitochondria was further shown in the improved organization of the mitochondria in tissue from a cardiac disease subject treated with D-Arg-2'6'-Dmt-Lys-Phe-NH$_2$ as compared to mitochondria in tissue from a subject not treated with D-Arg-2'6'-Dmt-Lys-Phe-NH$_2$. FIGS. 5A-5B.

The results show that aromatic-cationic peptides such as D-Arg-2'6'-Dmt-Lys-Phe-NH$_2$ are useful for reducing the number of mitochondria with abnormal mitochondrial ultrastructure, and/or ameliorating abnormal mitochondrial ultrastructure, and maintaining mitochondrial organization in cardiac disease. It is anticipated that aromatic-cationic peptides such as D-Arg-2'6'-Dmt-Lys-Phe-NH$_2$ will have a similar effect on abnormal mitochondria ultrastructure in subjects with Barth Syndrome. As such, aromatic-cationic peptides of the present disclosure are useful in methods for the treatment of Barth Syndrome.

Example 4—Use of Aromatic-Cationic Peptides in the Treatment of Barth Syndrome

This example will demonstrate the use of aromatic-cationic peptides, such as D-Arg-2'6'-Dmt-Lys-Phe-NH$_2$, or a pharmaceutically acceptable salt thereof, such as acetate or trifluoroacetate salt, in the treatment of Barth Syndrome.
Methods Barth Syndrome patients will receive daily administrations of a therapeutically effective amount of aromatic-cationic peptide, such as D-Arg-2'6'-Dmt-Lys-Phe-NH$_2$, or a pharmaceutically acceptable salt thereof, such as acetate or trifluoroacetate salt. Peptides may be administered orally, topically, systemically, intravenously, subcutaneously, intraperitoneally, or intramuscularly according to methods known in the art. Subjects will be evaluated weekly for the presence and/or severity of signs and symptoms associated with Barth Syndrome, including, but not limited to, e.g., cardiomyopathy, skeletal muscle abnormalities, neutropenia, slow development, weak muscle tone, increased levels of organic acids in the urine and blood, and frequent bacterial infections. Treatments will be maintained until such a time as Symptoms of Barth Syndrome are ameliorated or eliminated.
Results It is predicted that Barth Syndrome subjects receiving therapeutically effective amounts of aromatic-cationic peptide, such as D-Arg-2'6'-Dmt-Lys-Phe-NH$_2$, or a pharmaceutically acceptable salt thereof, such as acetate or trifluoroacetate salt will display reduced severity or elimination of symptoms associated with Barth Syndrome.

These results will show that aromatic-cationic peptides, such as D-Arg-2'6'-Dmt-Lys-Phe-NH$_2$, or a pharmaceutically acceptable salt thereof, such as acetate or trifluoroacetate salt are useful in the treatment of Barth Syndrome. Accordingly, the peptides are useful in methods comprising administering aromatic-cationic peptides to a subject in need thereof for the treatment of Barth Syndrome.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for reducing the number of mitochondria with abnormal mitochondrial ultrastructure, ameliorating abnormal mitochondrial ultrastructure, or maintaining mitochondrial organization in a subject having Barth Syndrome, comprising administering to the subject a therapeutically effective amount of the peptide D-Arg-2'6'-Dmt-Lys-Phe-NH$_2$ or a pharmaceutically acceptable salt thereof.

2. The method of claim 1, wherein the peptide is administered daily for 6 weeks or more.

3. The method of claim 1, wherein the peptide is administered daily for 12 weeks or more.

4. The method of claim 1, wherein the subject is human.

5. The method of claim 1, wherein the peptide is administered orally, topically, systemically, intravenously, subcutaneously, intraperitoneally, or intramuscularly.

6. The method of claim 1, further comprising separately, sequentially or simultaneously administering a cardiovascular agent to the subject.

7. The method of claim 6, wherein the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, an α-receptor blocking drug, a sympathetic nerve inhibitor, a digitalis formulation, an inotrope, and an anti-hyperlipidemic drug.

8. The method of claim 1, wherein the pharmaceutically acceptable salt comprises acetate or trifluoroacetate salt.

* * * * *